United States Patent [19]

Suhonen et al.

[11] Patent Number: 5,226,435
[45] Date of Patent: Jul. 13, 1993

[54] FLAVORED DENTAL FLOSS AND METHOD

[75] Inventors: Christopher H. Suhonen, Providencia, Chile; John A. Kaminski, Newark, Calif.

[73] Assignee: Gillette Canada Inc., Kirkland, Canada

[21] Appl. No.: 809,625

[22] Filed: Dec. 17, 1991

Related U.S. Application Data

[63] Continuation-in-part of Ser. No. 740,824, Aug. 1, 1991, abandoned.

[51] Int. Cl.$^5$ ............................................. A61C 15/00
[52] U.S. Cl. ........................................ 132/321; 424/49
[58] Field of Search ...................... 132/321; 424/49, 52

[56] References Cited

U.S. PATENT DOCUMENTS

| | | | |
|---|---|---|---|
| 174,619 | 3/1876 | Clark, Jr. | 132/321 |
| 660,943 | 10/1900 | Meister | 427/2 |
| 2,061,559 | 11/1936 | Brown et al. | 57/236 |
| 2,700,636 | 1/1955 | Ashton | 424/54 |
| 2,748,781 | 6/1956 | Collat | 132/325 |
| 3,330,732 | 7/1967 | Muhler | 424/49 |
| 3,412,192 | 11/1968 | Clapson | 264/280 |
| 3,492,131 | 1/1970 | Schlatter | 426/548 |
| 3,615,671 | 10/1971 | Shoaf et al. | 426/96 |
| 3,642,491 | 2/1972 | Schlatter | 426/548 |
| 3,699,979 | 10/1972 | Muhler et al. | 132/321 |
| 3,771,536 | 11/1973 | Dragon | 132/321 |
| 3,800,046 | 3/1974 | Schlatter | 426/548 |
| 3,800,812 | 4/1974 | Jaffe | 132/321 |
| 3,830,246 | 8/1974 | Gillings | 132/321 |
| 3,837,351 | 9/1974 | Thornton | 132/321 |

(List continued on next page.)

FOREIGN PATENT DOCUMENTS

| | | |
|---|---|---|
| 080440 | 1/1983 | European Pat. Off. . |
| 335466 | 10/1989 | European Pat. Off. . |
| 2606533 | 8/1976 | Fed. Rep. of Germany . |
| 2216803 | 10/1989 | United Kingdom . |

OTHER PUBLICATIONS

The Merck Index, Rahway; Merck & Co., Inc.; 1989, Eleventh Edition pp. 132 and 1591.

*Science,* (Oct. 2, 1970), vol. 170, pp. 81 & 82, "Aspartyl-phenylalanine Methyl Ester: A Low Calorie Sweetener" Marion R. Cloninger et al.

*Jada,* (Nov. 1985), vol. 111, pp. 745-751; Articles; Makinen-Others: "Comparison of Dentifrices with Different Sugar Alcohols".

*Primary Examiner*—John J. Wilson
*Attorney, Agent, or Firm*—Oblon, Spivak, McClelland, Maier and Neustadt

[57] ABSTRACT

A process for making a flattened, highly flavored floss and the floss product of that process. The process comprises coating a multi-filament thread with a first liquid or semi-solid wax composition having a high melting temperature and cooling the coating to a temperature at which the first wax composition has become a soft solid. The thread is flattened and coated with a lower melting liquid or semi-solid wax composition having a temperature less then the melting point of the first coating without disrupting the first wax composition of the flattened configuration of the thread. The lower melting wax composition contains volatile flavoring oil. Preferably, the inner wax composition is a microcrystalline wax and the outer wax composition comprises waxy a major portion of a polyethylene glycol having an average molecular weight at least 7000 daltons and an amount of a lower weight material such as an a liquid polyethylene glycol or an emulsifying wax to provide a coating which is liquid at a temperature of from 50° to 65° C. and which is solid at temperatures below about 50° C. Flavored coating compositions comprising flavoring oil and xylitol are also disclosed.

19 Claims, 2 Drawing Sheets

U.S. PATENT DOCUMENTS

| | | | |
|---|---|---|---|
| 3,838,702 | 10/1974 | Standish et al. | 132/321 |
| 3,897,795 | 8/1975 | Engel | 132/321 |
| 3,929,988 | 12/1975 | Barth | 424/54 |
| 3,939,261 | 2/1976 | Barth | 424/49 |
| 3,943,949 | 3/1976 | Ashton et al. | 132/321 |
| 4,029,113 | 6/1977 | Guyton | 132/321 |
| 4,033,365 | 7/1977 | Klepak et al. | 132/321 |
| 4,071,615 | 1/1978 | Barth | 424/52 |
| 4,153,732 | 5/1979 | Muhler et al. | 424/49 |
| 4,157,386 | 6/1979 | La Rochelle | 424/52 |
| 4,291,017 | 9/1981 | Beierle et al. | 424/52 |
| 4,414,990 | 11/1983 | Yost | 132/321 |
| 4,432,114 | 2/1984 | Goudsmit | 424/49 |
| 4,548,219 | 10/1985 | Newman et al. | 424/52 |
| 4,627,975 | 12/1986 | Lynch | 424/49 |
| 4,638,823 | 1/1987 | Newman et al. | 132/321 |
| 4,646,766 | 3/1987 | Stallard | 132/325 |
| 4,801,535 | 1/1989 | Babler et al. | 435/16 |
| 4,911,927 | 3/1990 | Hill et al. | 132/323 |
| 4,963,346 | 10/1990 | Amer | 424/49 |
| 4,971,797 | 11/1990 | Cherukuri et al. | 424/49 |
| 4,976,954 | 12/1990 | Kleber et al. | 424/52 |
| 4,983,404 | 1/1991 | Raman et al. | 426/3 |
| 4,986,288 | 1/1991 | Kent et al. | 132/321 |
| 4,996,056 | 2/1991 | Blass | 132/321 |
| 4,998,978 | 3/1991 | Varum | 132/321 |

FLAVORED DENTAL FLOSS AND METHOD

RELATIONSHIP TO COPENDING APPLICATION

This application is a continuation-in-part of copending application Ser. No. 07/740,824 filed Aug. 1, 1991, now abandoned.

FIELD OF THE INVENTION

This invention relates to an improved, flavored, waxed dental floss having a flattened cross-section and a highly flavored coating for cleaning the interproximal surfaces of teeth. This invention further relates to a process for manufacturing the improved article.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes and any similar article.

Dental flosses made of multiple filaments twisted to form a thread and coated with microcrystalline waxes to prevent fraying during manufacture and use are well-known. Sliding circular cross-sectioned flosses between closely spaced teeth in the scrapping cleaning action is sometimes difficult.

Flavoring flosses by adding flavoring oils to a wax coating mixture is also known. However, the wax coating mixtures must be heated to temperatures of around 80° C. or higher to provide a viscosity suitable for coating floss. The flavoring oils vaporize and rapidly oxidize at these high temperatures, producing flosses with odors but little residual taste of the original flavoring oils, even when excess amounts of flavoring oils are added to the coating mixture. Furthermore, the residual flavors remaining in the coating are degraded and bitter, not the fresh flavors desired.

Concentrated flavoring oils must be combined with sweeteners to provide palatable flavors. Conventional polysaccharides used as sweeteners promote caries forming bacteria.

OBJECTS AND SUMMARY OF THE INVENTION

It is an object of this invention to provide a wax coated, highly flavored floss with a flattened configuration.

It is a further object of this invention to provide a process which uses a high melting temperature wax coating to maintain a floss in a flattened configuration and an outer low melting temperature, highly flavored, waxy composition to provide a highly flavored coating without significantly disturbing the integrity of the primary wax coating or the flattened configuration of the floss.

It is another object of this invention to provide flavored coatings sweetened with xylitol to reduce growth of caries forming bacteria.

The flattened, highly flavored interproximal dental cleaning article of this invention comprises a plurality of filaments of a substrate material formed into a flattened thread, the flattened thread being coated and maintained in the flattened configuration by an inner wax coating having a melting temperature of above about 60° C. The inner wax coating is at least partially covered by an outer wax coating having a melting temperature below the melting temperature of the inner wax coating, the outer wax coating containing volatile flavoring oils.

The process of this invention for making a flattened, highly flavored interproximal dental cleaning article comprises first coating a plurality of filaments of a substrate material formed into a larger thread with a first liquid or semi-solid wax composition having a temperature above about 60° C. The coating is cooled to a temperature at which the first wax composition has solidified, and the thread is flattened. The flattened thread is then coated with a second liquid or semi-solid wax composition having a temperature less than the melting temperature of the first wax composition, the wax composition containing a volatile flavoring oil. The second wax composition is then solidified to form a flattened, highly flavored dental cleaning article.

Preferably, the outer or second wax composition comprises polyethylene glycol and the inner or first wax composition is a microcrystalline wax. The outer wax composition can comprise a major amount of a waxy polyethylene glycol having an average molecular weight of at least 7000 daltons and a lower molecular weight material compatible therewith. The amount of the lower molecular weight material is sufficient to provide a coating composition having a melting temperature within the temperature range of from 50° to 65° C. and which is solid at a temperatures below about 50° C. Preferably, the outer wax composition contains from 20 to 70 wt. % of waxy polyethylene glycol having an average molecular weight of at least 7000 daltons and from 1 to 40 wt. % amount of a liquid polyethylene glycol or an emulsifying wax comprising a fatty acid ester. Optimally the outer wax composition contains liquid polyethylene glycol.

A flattened, interproximal dental cleaning article of this invention comprises a plurality of filaments of a substrate material formed into a twisted thread, coated with a solid waxy composition which is a solid at temperatures below about 50° C. and preferably below about 60° C., and flattened to have a width to thickness ratio of at least 2:1 and preferably at least 4:1.

A process of this invention for preparing a flattened, twisted dental cleaning article comprises coating a plurality of filaments formed into a larger, twisted thread with a liquid or semi-solid wax composition which is solid at temperatures below about 50° C. and preferably below about 60° C.; cooling the coating to a temperature at which the coating is solid; and flattening the thread to a width to thickness ratio of at least 2:1 and preferably at least 4:1.

A preferred flavored interproximal dental cleaning article of this invention comprises a substrate material formed into a thread or tape having a flavored coating, the flavoring in the coating consisting essentially of flavoring oil and xylitol.

DETAILED DESCRIPTION OF THE INVENTION

The dental cleaning article of this invention is a wax coated, highly flavored floss having a flattened configuration. It is made by a process which uses a high melting temperature wax coating to maintain a flattened floss configuration and an outer low temperature melting highly flavored waxy composition to provide a highly flavored coating without significantly disturbing the integrity of the primary wax coating or the flattened configuration of the floss.

Figure 1:
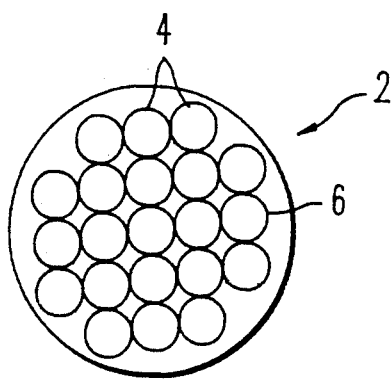
FIG. 1 is a cross-sectional representation of an intermediate thread formed according to this invention with a first wax coating.

FIG. 1 shows a cross-sectional representation of an intermediate thread 2 formed according to this invention with a first coating. The filaments 4 are bundled and preferably twisted into a thread, and coated with a primary coating 6.

The filaments are the substrate materials of the floss article. Suitable substrate filament materials include high and normal tenacity nylon such as nylon 6 and 66, rayon, Dacron, acetate polymers, polypropylene and the like as well as cotton, wool, silk, linen and other staple fibers. A plurality of individual filaments are formed together to give a larger thread having a sufficiently small diameter to permit insertion between the teeth. The preferred filaments are nylon, the filaments being twisted or otherwise woven together to make a non-fraying thread.

The inner or primary coating 6 is formed from a wax. Suitable waxes for this coating are preferably white or colorless and are solid at temperatures below 75° C. and preferably temperatures at or below 65° C. Suitable waxes include beeswax, paraffin and microcrystalline waxes, polyethylene glycols, wax-like resins and polymers, and mixtures thereof. They must remain sufficiently hard at the temperature of a secondary coating bath (50° to 65° C.) to retain the thread in a flattened configuration as will be explained in greater detail hereinafter.

Figure 2:
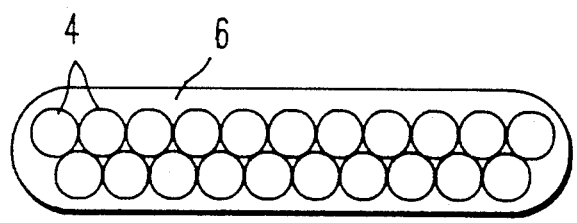
FIG. 2 is a cross-sectional representation of the flattened floss product of this invention, having a primary coating.

FIG. 2 is a cross-sectional representation of the flattened, flavored final floss product 8 of this invention. The floss 8 has been flattened and has an approximate width of from about 0.5 to 2 mm and preferably from 0.7 to 1.4 mm, a thickness of from about 0.1 to 0.4 mm, and a width to thickness ratio of from above 2:1 and preferably at least 4:1.

Figure 3:
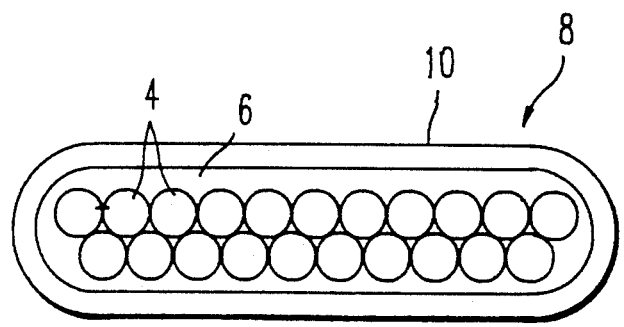
FIG. 3 is a cross-sectional representation of the flattened floss of FIG. 2, coated with a outer flavored coating.

FIG. 3 is the flattened floss of FIG. 2 with an outer flavored coating 10. The final floss product can have a weight suitable for flossing, for example, from 600 for thinner, narrower flosses to 1500 denier for thicker and wider flosses.

The outer or secondary flavored coating 10 is formed from a wax composition having a melting point below the melting point of the primary coating and a viscosity suitable for coating at the temperature of the secondary coating bath. It is preferably specially formulated with lower melting materials to provide the consistency, lubrication, and flexibility required for a non-flaking waxed dental floss. The outer or secondary flavored coating must be a liquid at temperatures of from 50° to 65° C. and be solid at temperatures below about 50° C.

The outer coating 10 is preferably formulated from a mixture of higher melting polyethylene glycol and a lower melting point emulsifying or solubilizing material compatible therewith. The lower melting point emulsifying material is selected and proportioned to provide the desired melting point but to yield a product which is solid at temperatures below 50° C. Preferably, the lower melting material softens the coating, increases its flexibility to reduce flaking, and increases the pliability of the coating.

A preferred outer coating mixture contains a major portion of a higher molecular weight polyethylene glycol and sufficient amounts of lower molecular weight, compatible compounds to yield a solid at temperatures below about 50° C. and a liquid at temperatures of about 50° to 65° C. Optimum mixtures are formulated with polyethylene glycols having a molecular weight of at least 7000 (PEG 8000 and Compound 20M, CARBOWAX ®, Union Carbide) which is solid at temperatures below about 60° C. mixed with lower melting materials having lower melting points, preferably of less than 30° C. Preferred low melting additives include liquid polyethylene glycols having molecular weight of less than 1000 daltons, optimally from 200 to 1000 daltons, and more complex emulsifying waxes such as PEG-40 sorbitan diisostearate (EMSORB 2726 ® PEG-40 sorbitan diisostearate, Henkel Corporation).

One preferred second coating wax composition comprises waxy polyethylene glycol having an average molecular weight from 7000 to 9000 daltons and an amount of a emulsifying wax comprising a fatty acid ester sufficient to provide melting and solidification temperatures in the desired ranges. The second wax composition can contain from 20 to 70 wt. % of waxy polyethylene glycol having an average molecular weight from 3000 to 20,000 daltons and from 1 to 40 wt. % emulsifying wax, for example.

The optimum second coating wax composition comprises waxy polyethylene glycol having an average molecular weight from 7000 to 9000 daltons and an amount of a liquid polyethylene glycol having a molecular weight of less than 1000 daltons to provide melting and solidification temperatures in the desired ranges. The second wax composition can contain from 20 to 70 wt. % of waxy polyethylene glycol having an average molecular weight from 3000 to 20,000 daltons and from 1 to 40 wt. % of a liquid polyethylene glycol such as polyethylene glycol having a molecular weight of 400 daltons (PEG 8), for example.

The outer coating also contains conventional flavoring materials such as flavoring oils and sweetening agents. Suitable flavors include peppermint, spearmint, wintergreen, cassia, cinnamon, menthol and the like; and fruit flavors such as cherry, strawberry, lime, and the like. Preferred sweeteners are high strength sweeteners such as saccharin, cyclamates, aspartame, xylitol and the like. The optimum sweetener is xylitol because it is a natural sugar useful in anticaries preparations.

Figure 4:
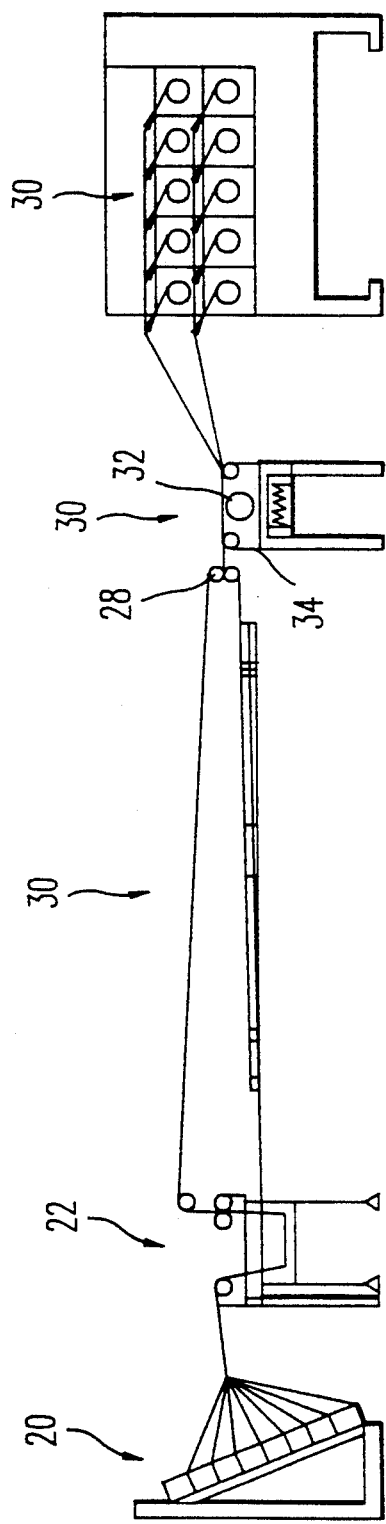
FIG. 4 is a schematic representation of the manufacturing process of this invention.

FIG. 4 is a schematic representation of the manufacturing process of this invention. Uncoated, twisted threads are stored on creel system 20. Threads from individual creels are drawn through a hot wax applicator bath 22 where the first coating is applied and rollers 24 where the excess coating is removed. The hot wax applicator bath 22 is preferably a jacketed, constant temperature bath of a microcrystalline wax having a temperature of above 60° C., preferably above 70° C. and optimally about 75°–85° C. The coated threads are then cooled as they pass through zone 26 to a soft solid, yielding the intermediate coated thread of FIG. 1. The threads are then flattened, for example, by passing them between rollers 28 spaced to provide the desired thickness, the primary coating material retaining the thread in the flattened configuration as shown in FIG. 2.

The flattened threads are then passed through the secondary coating station 30 where a secondary coating is applied, for example with a lick roller 32 immersed in the flavored coating composition in the jacketed heated bath 34. The flattened threads pass over the top of the roller, coating the threads with the coating material. The outer coating is then solidified, yielding the flattened flosses of FIG. 3. The flattened flosses are then wound onto creels 36. The creels are transferred to a bobbin winding machine (not shown) where the flattened, flavored flosses are wound onto bobbins.

The invention is further shown by the following specific but non-limiting examples.

EXAMPLE 1

A preferred secondary coating formulation is prepared as follows: To a 6 liter pot, polyethylene glycol having a molecular weight of approximately 8000 (2200 g, PEG 8000) is heated until liquified and cooled to 65° C.

In a second vessel, sorbitol (100 g, 70% USP) is heated and mixed with sodium saccharin (25 g).

In a third vessel, the flavor components (1925 g, NOVILLE) are prepared. Peppermint and spearmint flavors are mixed, and menthol is added and stirred until dissolved. PEG 40 Sorbitan diisostearate (750 g, EM-SORB 2726® PEG-40 sorbitan diisostearate, Henkel Corporation)) plasticizer and the contents of the second vessel are then added and mixed until homogeneous. This mixture is then mixed with the contents of the 6 liter pot.

The resulting mixture is maintained at a wax bath temperature of 50° to 65° C. and applied to the threads as a secondary coating.

EXAMPLE 2

Following procedures according to Example 1, flattened floss coated with a primary coating of microcrystalline wax was coated with the following composition using polyethylene glycol 400 (PEG 8) as a melting point depressant in polyethylene glycol 8000 (PEG 8000) wax. The coated products exhibited improved flaking properties, that is, exhibited less flaking than the product of Example 1.

| Component | Concentration | |
|---|---|---|
| | Weight Percent | Per 5 Kg |
| Saccharin | 0.70 | 35 g |
| Ethanol (190/200 proof) | 2.00 | 100 g |
| NOVILLE Dental Flavor | 38.50 | 1925 g |
| PEG 8 | 15.00 | 750 g |
| PEG 8000 | 43.80 | 2190 G |

EXAMPLE 3

Following procedures according to Example 1, flattened floss coated with a primary coating of microcrystalline wax was coated with the following composition using polyethylene glycol 400 (PEG 8) as a melting point depressant in polyethylene glycol 8000 (PEG 8000) wax. The coated products exhibited improved flaking properties, that is, exhibited less flaking than the product of Example 1.

| Component | Concentration | |
|---|---|---|
| | Weight Percent | Per 5 Kg |
| Xylitol | 5.00 | 250 g |
| Ethanol (190/200 proof) | 2.00 | 100 g |
| Water | 2.00 | 100 g |
| NOVILLE Dental Flavor | 35.00 | 1750 g |
| PEG 8 | 14.00 | 700 g |
| PEG 8000 | 42.00 | 2100 G |

EXAMPLE 4

Following procedures according to Example 1, flattened floss coated with a primary coating of microcrystalline wax was coated with the following composition using polyethylene glycol 400 (PEG 8) as a melting point depressant in polyethylene glycol 8000 (PEG 8000) wax. The coated products exhibited improved flaking properties, that is, exhibited less flaking than the product of Example 1.

| Component | Concentration | |
|---|---|---|
| | Weight Percent | Per 5 Kg |
| Cyclamate | 5.00 | 250 g |
| Ethanol (190/200 proof) | 2.00 | 100 g |
| Water | 2.00 | 100 g |
| NOVILLE Dental Flavor | 35.00 | 1750 g |
| PEG 8 | 14.00 | 700 g |
| PEG 8000 | 42.00 | 2100 G |

We claim:
1. A process for making a flattened, highly flavored interproximal dental cleaning article comprising
   a) coating a plurality of filaments of a substrate material formed into a thread with a first liquid or semi-solid wax composition having a temperature above about 60° C.;
   b) cooling the coating to a temperature at which the first wax composition has solidified and flattening the thread;
   c) coating the flattened thread with a second liquid or semi-solid wax composition having a temperature less than the melting temperature of the first wax composition, the wax composition containing a volatile flavoring oil; and
   d) solidifying the second wax composition to form a flattened, highly flavored dental cleaning article.
2. A process of claim 1 wherein the second wax composition comprises polyethylene glycol.
3. A process of claim 1 wherein the first wax composition is a microcrystalline wax.
4. A process of claim 3 wherein the microcrystalline wax has a melting temperature of at least 60° C.
5. A process of claim 4 wherein the second wax composition comprises polyethylene glycol.
6. A process of claim 5 wherein the second wax composition comprises polyethylene glycol having an aver- age molecular weight of at least 7000 daltons and a sufficient amount of a lower melting composition compatible therewith to provide a mixture which is liquid at a temperature within the range of from about 50° to 65° C. and is solid at temperatures below about 50° C.

7. A process of claim 5 wherein the second wax composition contains from 20 to 70 wt. % of polyethylene glycol having an average molecular weight from 7000 to 20,000 daltons and an amount of a liquid polyethylene glycol having molecular weight of less than 1000 daltons sufficient to provide coating which is a liquid at a temperature within the range of 50° to 65° C. and is a solid at a temperatures below about 50° C.

8. A process of claim 5 wherein the second wax composition contains from 20 to 70 wt. % of polyethylene glycol having an average molecular weight from 7000 to 20,000 daltons and an amount of a emulsifying wax comprising a fatty acid ester sufficient to provide coating which is a liquid at a temperature within the range of from 50° to 65° C. and is a solid at a temperatures below about 50° C.

9. A flattened, highly flavored interproximal dental cleaning article comprising a plurality of filaments of a substrate material formed into a flattened thread, the flattened thread being coated and maintained in the flattened configuration by an inner wax coating having a melting temperature of at least about 60° C., the inner wax coating being at least partially covered by an outer wax coating having a melting temperature below the melting temperature of the inner wax coating, the outer wax coating containing volatile flavoring oil.

10. A dental cleaning article of claim 9 wherein the outer wax coating comprises polyethylene glycol.

11. A dental cleaning article of claim 9 wherein the inner wax coating is a microcrystalline wax.

12. A dental cleaning article of claim 11 wherein the microcrystalline wax has a melting point of at least about 60° C.

13. A dental cleaning article of claim 12 wherein the outer wax coating comprises polyethylene glycol.

14. A dental cleaning article of claim 12 wherein the outer wax coating comprises a major amount of polyethylene glycol having an average molecular weight at least 7000 daltons and an amount of a lower molecular weight material compatible therewith to provide a coating composition having a melting temperature within the temperature range of from 50° to 65° C. and which is solid at a temperatures below about 50° C.

15. A dental cleaning article of claim 12 wherein the outer wax coating contains from 20 to 70 wt. % of waxy polyethylene glycol having an average molecular weight of at least 7000 daltons and from 1 to 40 wt. % amount of an liquid polyethylene glycol having a molecular weight of less than 1000 daltons.

16. A dental cleaning article of claim 12 wherein the outer wax coating contains from 20 to 70 wt. % of waxy polyethylene glycol having an average molecular weight of at least 7000 daltons and from 1 to 40 wt. % amount of an emulsifying wax comprising a fatty acid ester.

17. A process for preparing a flattened, twisted dental cleaning article comprising
a) coating a plurality of filaments formed into a twisted thread with a liquid or semi-solid wax composition which solid at temperatures below about 50° C.;
b) cooling the coating to a temperature at which the coating is solid; and
c) flattening the thread to form a flattened thread having a width to thickness ratio of at least 2:1.

18. A process of claim 17 wherein the wax composition is solid at temperatures below about 60° C.

19. A process of claim 17 wherein the width to thickness ratio is at least 4:1.

* * * * *